(12) United States Patent
Bollinger

(10) Patent No.: US 9,597,201 B2
(45) Date of Patent: Mar. 21, 2017

(54) PATIENT-SPECIFIC ACETABULAR GUIDE FOR ANTERIOR APPROACH

(71) Applicant: Biomet Manufacturing, LLC., Warsaw, IN (US)

(72) Inventor: Mark A. Bollinger, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/854,497

(22) Filed: Sep. 15, 2015

(65) Prior Publication Data

US 2016/0008144 A1 Jan. 14, 2016

Related U.S. Application Data

(63) Continuation of application No. 13/790,770, filed on Mar. 8, 2013, now Pat. No. 9,204,977, which is a continuation-in-part of application No. 13/711,306, filed on Dec. 11, 2012, now Pat. No. 9,060,788.

(51) Int. Cl.
| | |
|---|---|
| *A61F 2/46* | (2006.01) |
| *A61B 17/17* | (2006.01) |
| *A61B 17/88* | (2006.01) |
| *A61B 17/56* | (2006.01) |

(52) U.S. Cl.
CPC ........ *A61F 2/4609* (2013.01); *A61B 17/1746* (2013.01); *A61B 17/8872* (2013.01); *A61B 34/10* (2016.02); *A61B 2017/568* (2013.01); *A61B 2034/108* (2016.02)

(58) Field of Classification Search
CPC . A61B 17/17; A61B 17/8872; A61B 17/1746; A61F 2/4609

USPC .............................. 606/91; 623/21.18–22.11
See application file for complete search history.

(56) References Cited

U.S. PATENT DOCUMENTS

| | | | |
|---|---|---|---|
| 1,480,285 | A | 1/1924 | Moore |
| 2,181,746 | A | 11/1939 | Siebrandt |
| 2,407,845 | A | 9/1946 | Orisan |
| 2,416,228 | A | 2/1947 | Sheppard |
| 2,618,913 | A | 11/1952 | Plancon et al. |
| 2,910,978 | A | 11/1959 | Urist |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

"U.S. Appl. No. 14/204,910, Non Final Office Action mailed Jan. 14, 2016", 10 pgs.

(Continued)

*Primary Examiner* — Christopher Beccia
(74) *Attorney, Agent, or Firm* — Schwegman Lundberg & Woessner, P.A.

(57) ABSTRACT

An orthopedic device includes a patient-specific acetabular guide that can be used for preparing an acetabulum of a patient to receive an acetabular implant. The acetabular guide has a body with an outer three-dimensional surface configured to match an acetabulum of a specific patient's hip joint designed from data of the patient's hip joint. The acetabular guide can further include a peripheral annular rim.

20 Claims, 10 Drawing Sheets

(56) References Cited

U.S. PATENT DOCUMENTS

| | | |
|---|---|---|
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 4,994,064 A | 2/1991 | Aboczky |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen et al. |
| 5,030,221 A | 7/1991 | Buechel et al. |
| 5,037,424 A | 8/1991 | Aboczsky |
| 5,041,117 A | 8/1991 | Engelhardt |
| 5,053,037 A | 10/1991 | Lackey |
| 5,053,039 A | 10/1991 | Hofmann et al. |
| 5,056,351 A | 10/1991 | Stiver et al. |
| 5,061,270 A | 10/1991 | Aboczky |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,141,512 A | 8/1992 | Farmer et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,571,111 A | 11/1996 | Aboczky |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,616,147 A | 4/1997 | Gadelius |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |

(56) References Cited

U.S. PATENT DOCUMENTS

| | | |
|---|---|---|
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,013,081 A | 1/2000 | Burkinshaw et al. |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,187,010 B1 | 2/2001 | Masini |
| 6,195,615 B1 | 2/2001 | Lysen |
| 6,203,546 B1 | 3/2001 | Macmahon |
| 6,205,411 B1 | 3/2001 | Digioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,424,332 B1 | 7/2002 | Powell |
| 6,427,698 B1 | 8/2002 | Yoon et al. |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert et al. |
| 6,696,073 B2 | 2/2004 | Boyce et al. |
| 6,697,664 B2 | 2/2004 | Kienzle, III et al. |
| 6,699,289 B2 | 3/2004 | Iannotti et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,743,235 B2 | 6/2004 | Subba Rao |
| 6,749,638 B1 | 6/2004 | Saladiono |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |

(56) References Cited

U.S. PATENT DOCUMENTS

| | | |
|---|---|---|
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | Mclean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De La Barrera |
| 7,419,492 B2 | 9/2008 | Yoon et al. |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian et al. |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-schäffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,690 B2 | 11/2010 | Metzger |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roβner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,172,850 B2 | 5/2012 | Mcminn |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaβky et al. |
| 8,313,491 B2 | 11/2012 | Green, II et al. |
| D672,038 S | 12/2012 | Frey |
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |

(56) References Cited

U.S. PATENT DOCUMENTS

| | | |
|---|---|---|
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 * | 9/2014 | Perez ............... A61F 2/30734 606/91 |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 9,005,297 B2 | 4/2015 | Katrana et al. |
| 9,060,788 B2 | 6/2015 | Bollinger |
| 9,066,734 B2 | 6/2015 | Schoenefeld et al. |
| 9,107,139 B2 | 8/2015 | Sirotkin et al. |
| 9,204,977 B2 | 12/2015 | Bollinger |
| 2001/0005797 A1 | 6/2001 | Barlow et al. |
| 2001/0011190 A1 | 8/2001 | Park |
| 2001/0021876 A1 | 9/2001 | Terril-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson, Jr. et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny, III |
| 2004/0220583 A1 | 11/2004 | Pieczynski, II et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La Barrera |
| 2005/0113841 A1 | 5/2005 | Sheldon et al. |
| 2005/0113846 A1 | 5/2005 | Carson |
| 2005/0119664 A1 * | 6/2005 | Carignan ............ A61F 2/30942 606/96 |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams, III et al. |
| 2005/0234461 A1 | 10/2005 | Burdulis, Jr. et al. |
| 2005/0234465 A1 | 10/2005 | Mccombs et al. |

(56) References Cited

U.S. PATENT DOCUMENTS

| | | |
|---|---|---|
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0069444 A1 | 3/2006 | Deffenbaugh |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady, Jr. et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |

(56) References Cited

U.S. PATENT DOCUMENTS

| | | |
|---|---|---|
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262499 A1 | 10/2008 | Giori et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |

(56) References Cited

U.S. PATENT DOCUMENTS

| | | |
|---|---|---|
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276053 A1 | 11/2011 | Birkbeck et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch et al. |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1* | 6/2012 | Iannotti ............ A61B 17/1746 606/86 R |
| 2012/0150242 A1 | 6/2012 | Mannion |
| 2012/0158002 A1 | 6/2012 | Carignan et al. |
| 2012/0165954 A1 | 6/2012 | Nimal |
| 2012/0190971 A1 | 7/2012 | De Wekker |
| 2012/0192401 A1 | 8/2012 | Pavlovskaia et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0245647 A1 | 9/2012 | Kunz et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2012/0330319 A1 | 12/2012 | Birkbeck et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0072940 A1* | 3/2013 | Dawood ............ A61B 17/1746 606/91 |
| 2013/0085500 A1 | 4/2013 | Meridew et al. |
| 2013/0085590 A1 | 4/2013 | Bryan et al. |
| 2013/0110116 A1 | 5/2013 | Kehres et al. |
| 2013/0110470 A1 | 5/2013 | Vanasse et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1* | 9/2013 | Bettenga ............ A61B 17/1666 606/91 |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0292870 A1 | 11/2013 | Roger |

(56) References Cited

U.S. PATENT DOCUMENTS

| | | |
|---|---|---|
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenfeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0150688 A1 | 6/2015 | Vanasse et al. |
| 2015/0157341 A1 | 6/2015 | Catanzarite et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A2 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A1 | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6233790 A | 8/1994 |
| JP | 2000245758 A | 9/2000 |
| JP | 2005218861 A | 8/2005 |
| JP | 2009514612 A | 4/2009 |
| JP | 2011505080 A | 2/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| TW | I231755 B | 5/2005 |
| TW | 201114409 A | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |

(56) References Cited

FOREIGN PATENT DOCUMENTS

| | | |
|---|---|---|
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A2 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013170872 A1 | 11/2013 |
| WO | WO-2014019712 A1 | 2/2014 |
| WO | WO-2014093435 A1 | 6/2014 |
| WO | WO-2015084831 A1 | 6/2015 |

OTHER PUBLICATIONS

"Ascent Total Knee System", Biomet, Inc., (Oct. 31, 1999), 16 pgs.
"European Application Serial No. 13815628.6, Office Action mailed Jul. 22, 2015", 2 pgs.
"European Application Serial No. 13815628.6, Response filed Feb. 1, 2016 to Office Action mailed Jul. 22, 2015", 8 pgs.
"International Application Serial No. PCT/US2012/060848, International Search Report mailed Apr. 12, 2013", 6 pgs.
"International Application Serial No. PCT/US2012/060853, International Search Report mailed Apr. 9, 2013", 6 pgs.
"International Application Serial No. PCT/US2013/067505, Invitation to Pay Additional Fees mailed Feb. 6, 2014", 6 pgs.
BIOMET, "The Oxford® Partial Knee System Surgical Technique", Biomet: Manual of the Surgical Technique, (Feb. 2010), 44 pgs.
"3D-Implantatplanung und StereolithographieImplantatbohrschablonen", Stomatologie 101.3, (2004), 55-59.
"Amazing Precision. Beautiful Results. The next evolution of MAKOplasty® is here", MAKO Surgical Corp., (Feb. 2009), 6 pgs.
"U.S. Appl. No. 13/790,770, Final Office Action mailed May 18, 2015", 9 pgs.
"U.S. Appl. No. 13/790,770, Non Final Office Action mailed Dec. 26, 2014", 9 pgs.
"U.S. Appl. No. 13/790,770, Notice of Allowance mailed Aug. 5, 2015", 5 pgs.
"U.S. Appl. No. 13/790,770, Response filed Apr. 22, 2015 to Non Final Office Action mailed Dec. 26, 2014", 14 pgs.
"U.S. Appl. No. 13/790,770, Response filed Jul. 17, 2015 to Final Office Action mailed May 18, 2015", 7 pgs.
"Ascent™ Total Knee System", Biomet, Inc., (Oct. 31, 1999), 16 pgs.
"Australian Application Serial No. 2013222609, First Examiner Report mailed Feb. 16, 2015", 5 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"European Application Serial No. 07809326.7, Examination Notification Art. 94(3) mailed Jan. 22, 2015", 6 pgs.
"European Application Serial No. 07809326.7, Extended European Search Report mailed Nov. 15, 2011", 6 pgs.
"European Application Serial No. 09731923.0, Examination Notification Art. 94(3) mailed Feb. 10, 2015", 7 pgs.
"European Application Serial No. 10705064.3, Examination Notification Art. 94(3) mailed Feb. 4, 2015", 6 pgs.
"European Application Serial No. 12724475.4, Examination Notification Art. 94(3) mailed Nov. 24, 2014", 7 pgs.
"Great Britain Application Serial No. 1116054.6, Search Report mailed Dec. 21, 2011".
"Great Britain Application Serial No. 1207103.1, Office Action mailed May 14, 2015".
"Hipsextant Instructions of Use", Surgical Planning Associates, Inc., (2011), 19 pgs.
"International Application Serial No. PCT/EP2010/061630, International Search Report mailed Nov. 30, 2010", 3 pgs.
"International Application Serial No. PCT/US2007/013223, International Preliminary Report on Patentability mailed Dec. 24, 2008", 5 pgs.
"International Application Serial No. PCT/US2007/013223, International Search Report mailed Nov. 26, 2007".
"International Application Serial No. PCT/US2007/013223, Written Opinion mailed Nov. 26, 2007", 4 pgs.
"International Application Serial No. PCT/US2009/039507, International Preliminary Report on Patentability mailed Oct. 28, 2010", 9 pgs.
"International Application Serial No. PCT/US2009/039507, International Search Report mailed Jul. 14, 2009", 6 pgs.
"International Application Serial No. PCT/US2009/039507, Written Opinion mailed Jul. 14, 2009", 7 pgs.
"International Application Serial No. PCT/US2009/039578, International Preliminary Report on Patentability mailed Oct. 28, 2010", 9 pgs.
"International Application Serial No. PCT/US2009/039578, International Search Report mailed Jul. 31, 2009", 6 pgs.
"International Application Serial No. PCT/US2009/039578, Written Opinion mailed Jul. 31, 2009", 7 pgs.

(56) References Cited

OTHER PUBLICATIONS

"International Application Serial No. PCT/US2009/056670, International Preliminary Report on Patentability mailed Mar. 31, 2011", 12 pgs.
"International Application Serial No. PCT/US2009/056670, International Search Report mailed Mar. 2, 2010", 7 pgs.
"International Application Serial No. PCT/US2009/056670, Invitation to Pay Additional Fees and Partial Search Report mailed Nov. 26, 2009".
"International Application Serial No. PCT/US2009/056670, Written Opinion mailed Mar. 2, 2010", 10 pgs.
"International Application Serial No. PCT/US2010/024073, International Preliminary Report on Patentability mailed Aug. 25, 2011", 8 pgs.
"International Application Serial No. PCT/US2010/024073, International Search Report mailed Jun. 4, 2010", 4 pgs.
"International Application Serial No. PCT/US2010/024073, Written Opinion mailed Jun. 4, 2010", 6 pgs.
"International Application Serial No. PCT/US2010/024579, International Preliminary Report on Patentability mailed Sep. 1, 2011", 7 pgs.
"International Application Serial No. PCT/US2010/024579, International Search Report mailed Arp. 22, 2010", 3 pgs.
"International Application Serial No. PCT/US2010/024579, Written Opinion mailed Apr. 22, 2010", 5 pgs.
"International Application Serial No. PCT/US2010/024584, International Preliminary Report on Patentability mailed Sep. 1, 2011", 8 pgs.
"International Application Serial No. PCT/US2010/024584, International Search Report mailed Aug. 19, 2010", 6 pgs.
"International Application Serial No. PCT/US2010/024584, Written Opinion mailed Aug. 19, 2010", 6 pgs.
"International Application Serial No. PCT/US2010/038177, International Preliminary Report on Patentability mailed Dec. 22, 2011", 10 pgs.
"International Application Serial No. PCT/US2010/038177, International Search Report mailed Aug. 24, 2010", 4 pgs.
"International Application Serial No. PCT/US2010/038177, Written Opinion mailed Aug. 24, 2010", 8 pgs.
"International Application Serial No. PCT/US2010/038845, International Preliminary Report on Patentability mailed Jan. 5, 2012", 9 pgs.
"International Application Serial No. PCT/US2010/038845, International Search Report mailed Oct. 5, 2010", 4 pgs.
"International Application Serial No. PCT/US2010/038845, Written Opinion mailed Oct. 5, 2010", 7 pgs.
"International Application Serial No. PCT/US2010/050701, International Preliminary Report on Patentability mailed Apr. 12, 2012", 10 pgs.
"International Application Serial No. PCT/US2010/050701, International Search Report mailed Oct. 7, 2010", 6 pgs.
"International Application Serial No. PCT/US2010/050701, Written Opinion mailed Dec. 7, 2010", 8 pgs.
"International Application Serial No. PCT/US2011/026333, International Preliminary Report on Patentability mailed Sep. 7, 2012", 10 pgs.
"International Application Serial No. PCT/US2011/026333, International Search Report mailed Aug. 9, 2011", 6 pgs.
"International Application Serial No. PCT/US2011/026333, Invitation to Pay Additional Fees mailed May 3, 2011".
"International Application Serial No. PCT/US2011/026333, Written Opinion mailed Aug. 9, 2011", 8 pgs.
"International Application Serial No. PCT/US2011/026412, International Search Report mailed May 9, 2011", 5 pgs.
"International Application Serial No. PCT/US2011/026412, Written Opinion mailed May 9, 2011", 6 pgs.
"International Application Serial No. PCT/US2011/057300, International Search Report mailed Mar. 5, 2012", 7 pgs.
"International Application Serial No. PCT/US2011/057300, Written Opinion mailed Mar. 5, 2012", 9 pgs.
"International Application Serial No. PCT/US2012/026356, International Preliminary Report on Patentability mailed Sep. 6, 2013", 8 pgs.
"International Application Serial No. PCT/US2012/026356, International Search Report mailed May 8, 2012", 5 pgs.
"International Application Serial No. PCT/US2012/026356, Written Opinion mailed May 8, 2012", 6 pgs.
"International Application Serial No. PCT/US2012/038351, International Preliminary Report on Patentability mailed Nov. 28, 2013", 9 pgs.
"International Application Serial No. PCT/US2012/038351, Written Opinion mailed Jul. 6, 2012", 8 pgs.
"International Application Serial No. PCT/US2012/041893, International Search Report mailed Oct. 23, 2012", 5 pgs.
"International Application Serial No. PCT/US2012/042081, International Preliminary Report on Patentability mailed Jan. 3, 2014", 7 pgs.
"International Application Serial No. PCT/US2012/042081, Written Opinion mailed Sep. 5, 2012", 6 pgs.
"International Application Serial No. PCT/US2012/052853, International Preliminary Report on Patentability mailed Mar. 13, 2014", 13 pgs.
"International Application Serial No. PCT/US2012/052853, International Search Report mailed Nov. 15, 2012", 6 pgs.
"International Application Serial No. PCT/US2012/052853, Written Opinion mailed Nov. 15, 2012", 12 pgs.
"International Application Serial No. PCT/US2012/059189, International Preliminary Report on Patentability mailed Apr. 24, 2014", 10 pgs.
"International Application Serial No. PCT/US2012/059189, International Search Report mailed Dec. 18, 2012", 6 pgs.
"International Application Serial No. PCT/US2012/059189, Written Opinion mailed Dec. 18, 2012", 9 pgs.
"International Application Serial No. PCT/US2012/060842, International Preliminary Report on Patentability mailed May 8, 2014", 7 pgs.
"International Application Serial No. PCT/US2012/060842, International Search Report mailed Feb. 6, 2013", 4 pgs.
"International Application Serial No. PCT/US2012/060842, Written Opinion mailed Feb. 6, 2013", 5 pgs.
"International Application Serial No. PCT/US2012/060848, International Preliminary Report on Patentability mailed May 8, 2014", 11 pgs.
"International Application Serial No. PCT/US2012/060848, Invitation to Pay Additional Fees mailed Feb. 6, 2013".
"International Application Serial No. PCT/US2012/060848, Written Opinion mailed Apr. 12, 2013", 9 pgs.
"International Application Serial No. PCT/US2012/060853, International Preliminary Report on Patentability mailed May 8, 2014", 11 pgs.
"International Application Serial No. PCT/US2012/060853, Invitation to Pay Additional Fees mailed Feb. 7, 2013".
"International Application Serial No. PCT/US2012/060853, Written Opinion mailed Apr. 9, 2013", 9 pgs.
"International Application Serial No. PCT/US2012/060854, International Preliminary Report on Patentability mailed May 8, 2014", 8 pgs.
"International Application Serial No. PCT/US2012/060854, International Search Report mailed Feb. 6, 2013", 4 pgs.
"International Application Serial No. PCT/US2012/060854, Written Opinion mailed Feb. 6, 2013", 6 pgs.
"International Application Serial No. PCT/US2013/026875, International Preliminary Report on Patentability mailed Sep. 4, 2014", 9 pgs.
"International Application Serial No. PCT/US2013/026875, International Search Report mailed Jun. 7, 2013", 5 pgs.
"International Application Serial No. PCT/US2013/026875, Written Opinion mailed Jun. 7, 2013", 8 pgs.
"International Application Serial No. PCT/US2013/057097, International Preliminary Report on Patentability mailed Mar. 12, 2015", 10 pgs.
"International Application Serial No. PCT/US2013/057097, International Search Report mailed Oct. 14, 2013", 6 pgs.

(56) References Cited

OTHER PUBLICATIONS

"International Application Serial No. PCT/US2013/057097, Written Opinion mailed Oct. 14, 2013", 9 pgs.
"International Application Serial No. PCT/US2013/067505, International Search Report mailed Apr. 14, 2014", 5 pgs.
"International Application Serial No. PCT/US2013/067505, Written Opinion mailed Apr. 14, 2014", 11 pgs.
"International Application Serial No. PCT/US2013/074288, International Preliminary Report on Patentability mailed Jun. 25, 2015", 13 pgs.
"International Application Serial No. PCT/US2013/074288, International Search Report mailed May 23, 2014", 7 pgs.
"International Application Serial No. PCT/US2013/074288, Written Opinion mailed May 23, 2014", 11 pgs.
"International Application Serial No. PCT/US2014/022000, International Search Report mailed Jun. 24, 2014", 3 pgs.
"International Application Serial No. PCT/US2014/022000, Written Opinion mailed Jun. 24, 2014".
"International Application Serial No. PCT/US2014/023655, International Search Report mailed Jul. 10, 2014", 4 pgs.
"International Application Serial No. PCT/US2014/023655, Written Opinion mailed Jul. 10, 2014".
"International Application Serial No. PCT/US2014/068131, International Search Report mailed May 8, 2015", 5 pgs.
"International Application Serial No. PCT/US2014/068131, Written Opinion mailed May 8, 2015", 9 pgs.
"Is Subchondroplasty® Right for Me?", [Online] retrieved from the internet: <http://www.subchondroplast}'..com/about subchondroplast}'./is subchondroplasty right for >, (Jul. 1, 2013), 1 pg.
"Japanese Application Serial No. 2014511538, Office Action mailed Apr. 7, 2015".
"Knee tensor combined with laser femoral head locator", Research Disclosure, No. 507, (Jul. 2006), 903.
"Method for constructing an allograft sleeve", Research Disclosure, No. 476, (Dec. 2003), 1294 pgs.
"OSS™ Orthopaedic Salvage System, Femoral/Tibial Augmentation", Biomet Orthopedics, Inc.,, (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"Patient Matched PMIImplants, C.A.M.R.A. 3-D Imaging", brochure, Biomet, Inc., (Jan. 31, 1991), 6 pgs.
"Regenerex® Tibial Cone Augment, Surgical Technique Addendum to the Vanguard® SSK Revision System", Biomet® Orthopedics., (Mar. 31, 2010), 1-8.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Ortho edics, (2013), 1-13.
"Signature™ Personalized Patient Care, Surgical Technique Addendum to the Vanguard Knee System", Biomet® Orthopedics, Inc., (May 15, 2009), 1-8.
"Signature™ Personalized Patient Care, Surgical Technique Addendum Vanguard® Complete Knee System", Biomet® Orthopedics Brochure, (2011), 1-32.
"Subchondroplasty", [Online] retrieved from the internet: <http://www.subchondroplasty.com/>, (Jul. 1, 2013), 1 pg.
"The Oxford® Partial Knee Surgical Technique", Biomet, (Feb. 2010), 1-38.
"TruMatch™ Personalized knee replacement solutions", SIGMA® DePuy Orthopaedics, Inc., (2009), 2 pgs.
"Vanguard® PFR Partial Knee Patellofemoral Replacement System", Surgical Technique, Biomet Orthopaedics,, (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013).

"Zimmer® UniSpacer® Knee System", Zimmer, Inc., (2005), 4 pgs.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited 2011, 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use of Computerized Tomography in the Measurement of Glenoid Version", Journal of Bone & Joint Surgery Am. (JBJS) 1992;74, (Aug. 1992), 1032-1037.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Sugery, A New Paradigm", Techniques in Orthopaedics® vol. 18, No. 2 (2003), 221-229.
Hutmacher, Dietmar W, "Scaffolds in tissue engineering bone and cartilage", Biomaterials, 2000 Elsevier Science Ltd., (2000), 2529-2543.
Kaus, Michael R, "Automated Segmentation of MR Images of Brain Tumors", Radiology, vol. 218, No. 2,, (2001), 586-591.
Kelly, Todd C, "Role of Navigation in Total Hip Arthroplasty", The Journal of Bone & Joint Surgery(2009) vol. 91-A, Supplement 1, (2009), 153-8.
Klein, M, "Robot assisted insertion of craniofacial implants—clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.
Murphy, S B, et al., "The Hip Sextant: Navigation of Acetabular Component Orientation Using a Mechanical Instrument", (2009), 1 pg.
Nicholls, Paul M. D, "Trauma Grand Rounds PMI (Patient-Matched Implants)", Biomet Orthopedics, Inc. (Feb. 29, 2000), 1 pg.
Overhoff, H M, et al., "Total Knee Arthroplasty: Coordinate System Definition and Planning based on 3-D Ultrasound Image Volumes", CARS 2001, Elsevier Science B.V., (2001), 283-288.

(56) References Cited

OTHER PUBLICATIONS

Portheine, F., "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", (1998), 5 pgs.

Portheine, K, "Development of a clinical demonstrator for computer assisted orthopedic surgery with CT-image based individual templates", Computer Assisted Radiology and Surgery Elsevier Science B.V., (1997), 944-949.

Radermacher, "Computer Assisted Orthopaedic Surgery with Image Based Individual Templates", Clinical Orthopaedics and Related Research No. 354, Lippincott Williams & Wilkins, (Sep. 1998), 28-38.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

Radermacher, Klaus, et al., "Computer Assisted Orthopaedic Individual Templates", Clinical Orthopaedics and Related Research No. 354, (Sep. 1998), 28-38.

Schuller-Gotzburg, P, et al., "3D-Implantatplanung und Stereolithographie-Implantatbohrschablonen", Stomatologie 101.3, (May 2004), 55-59.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (Jul. 2006), 214-225.

Slammin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796& ISSUE . . . >, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Subburaj, K, et al., "Automated 3D Geometric Reasoning in Computer Assisted Joint Reconstructive Surgery", IEEE International Conference on Automation Science and Engineering, (2009), 367-372.

Thoma, W, "Endoprosthetic care of the knee joint based on a 3D computer chromatography subtraction process", Topic: Computer-aided orthopedic surgery. Orthopedist 2000 29: Springer Verlag, (2000), 641-644.

Thoma, W, et al., "Endoprothetischen Versorgung des Kniegelenks auf der Basis eines 3D-computertomographischen Subtraktionsverfahrens", (2000), 641-644.

"U.S. Appl. No. 13/711,306, Non Final Office Action mailed Sep. 23, 2014", 10 pgs.

"U.S. Appl. No. 13/711,306, Notice of Allowance mailed Feb. 17, 2015", 10 pgs.

"U.S. Appl. No. 13/711,306, Response filed Dec. 23, 2014 to Non Final Office Action mailed Sep. 23, 2014", 17 pgs.

"U.S. Appl. No. 14/204,910, Corrected Notice of Allowance mailed Sep. 16, 2016", 4 pgs.

"U.S. Appl. No. 14/204,910, Notice of Allowance mailed Aug. 22, 2016", 5 pgs.

"U.S. Appl. No. 14/204,910, Response filed Jul. 11, 2016 to Non Final Office Action mailed Jan. 14, 2016", 14 pgs.

* cited by examiner

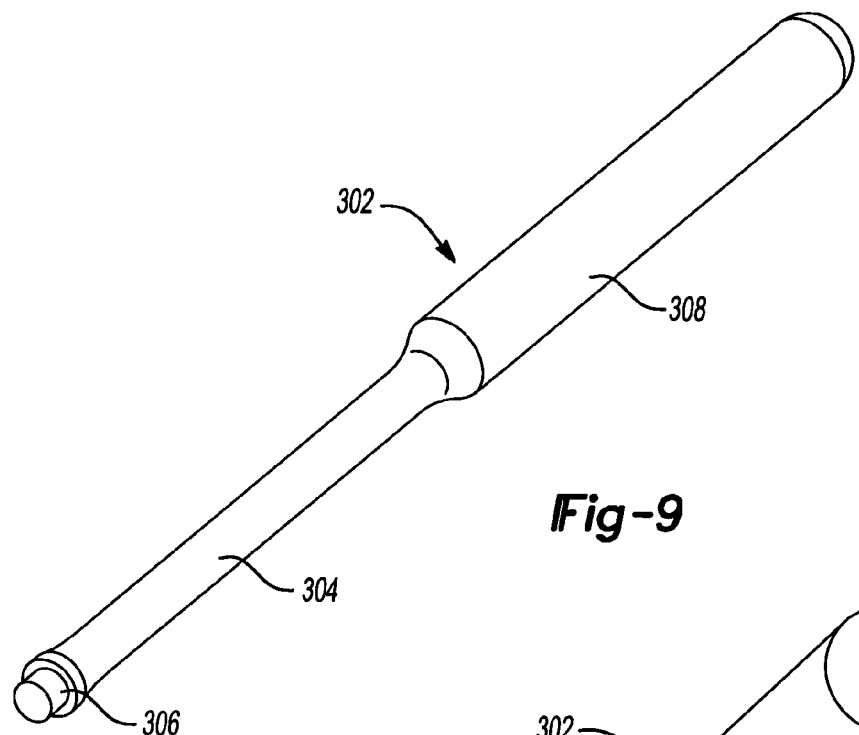
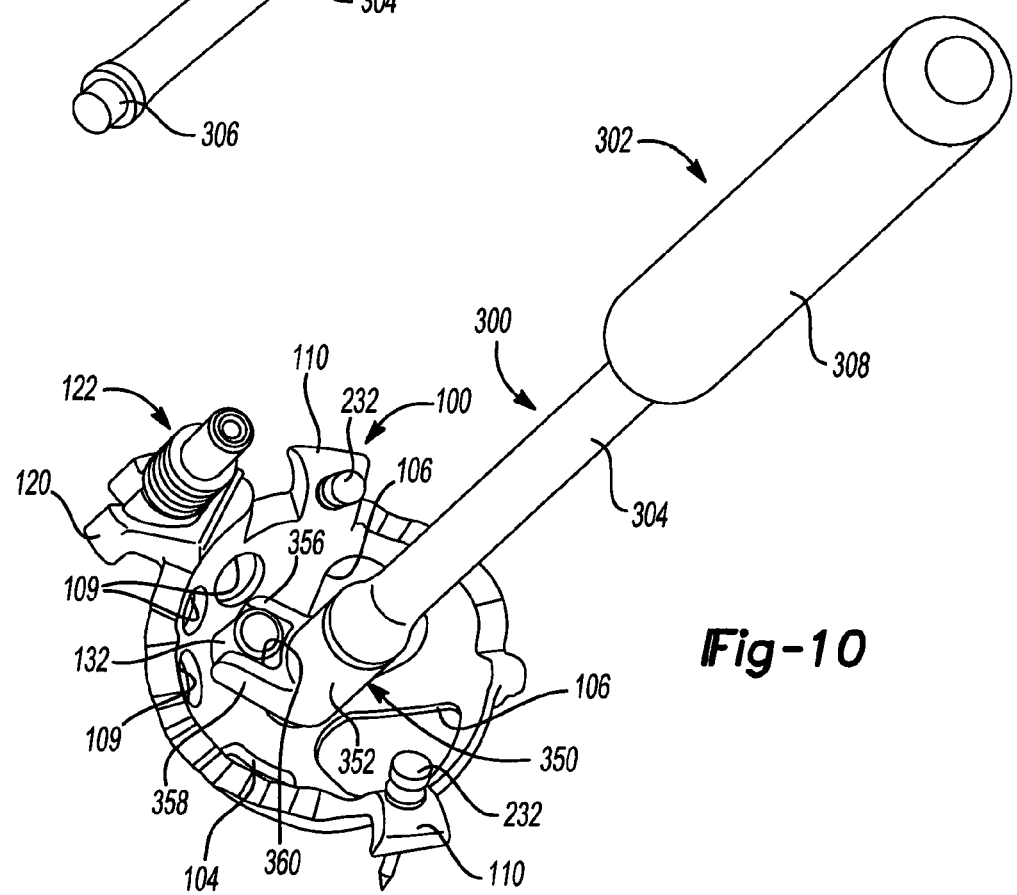

PATIENT-SPECIFIC ACETABULAR GUIDE FOR ANTERIOR APPROACH

CROSS-REFERENCE TO RELATED APPLICATIONS

This application is a continuation of U.S. patent application Ser. No. 13/790,770, filed on Mar. 8, 2013, which is a continuation-in-part of U.S. patent application Ser. No. 13/711,306, filed on Dec. 11, 2012, now issued as U.S. Pat. No. 9,060,788, entitled Patient-Specific Acetabular Guide for Anterior Approach. The entire disclosure of the above applications are incorporated herein by reference.

FIELD

The present teachings relate to an acetabular guide and particularly to a patient-specific guide and various associated instruments.

INTRODUCTION

The present teachings provide a patient-specific acetabular guide and associated instruments for implanting an acetabular implant into an acetabulum of a patient for hip joint arthroplasty.

SUMMARY

The present teachings provide various instruments and methods for generally preparing the acetabulum of a patient to receive an acetabular implant, such as, for example, an acetabular cup along an alignment axis. The alignment axis and various patient-specific guides and other associated instruments can be designed during a pre-operative plan using a three-dimensional reconstruction of the patient's relevant anatomy, such as the pelvis or portions thereof, including the acetabular and periacetabular areas of the pelvis. The three-dimensional reconstruction can be based on medical images, including MRI, CT, ultrasound, or X-ray scans and prepared using commercially available imaging software.

The present teachings provide, for example, a patient-specific acetabular guide that can be used for preparing an acetabulum of a patient to receive an acetabular implant, such as an acetabular cup. The acetabular guide has a dome-shaped body with a peripheral annular rim and an outer three-dimensional surface configured to match an acetabulum of a specific patient's hip joint from three-dimensional medical images of the patient's hip joint during a preoperative plan for the patient. A patient-specific registration guide can be permanently or removably attached to the peripheral rim. The patient-specific registration guide has a longitudinal bore defining a patient-specific alignment axis with an alignment orientation configured for guiding an acetabular implant for the patient during the preoperative plan of the patient. The registration guide has a patient-specific undersurface configured to mate with a corresponding portion of a periacetabular surface and/or acetabular rim surface of the acetabulum of the patient.

In some embodiments, the acetabular guide can include a plurality of spaced-apart registration hooks. Each registration hook can extend from and be attached to the peripheral rim of the acetabular guide. Each registration hook has a patient-specific undersurface configured to mate with a corresponding surface of the acetabular rim of the patient's acetabulum.

The present teachings also provide a method for hip joint arthroplasty. The method includes inserting a patient-specific acetabular guide into an acetabulum of a patient. A patient specific undersurface of a dome-shaped body of the acetabular guide mates substantially as negative of a corresponding surface of the acetabulum. At least one patient-specific registration hook extends from a peripheral rim of the acetabular guide over a portion of an acetabular rim of the acetabulum. The method includes inserting an alignment pin into the patient's bone through a bore of a patient-specific registration guide. The patient-specific registration guide is removably attached to the peripheral rim of the acetabular guide. The patient-specific registration guide is preoperatively configured to define a patient-specific alignment orientation for inserting an acetabular implant. The method includes removing the acetabular guide without removing the alignment pin and inserting an acetabular implant along an orientation parallel to the alignment pin.

In some embodiments, the acetabular guide can be inserted into the acetabulum using an inserter with a removable adapter element. A distal bore of the adapter element can be coupled to a first post of the acetabular guide. A second post of the acetabular guide can held between first and second flanges extending from the adapter element.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 9 is an isometric view of the acetabular guide inserter of FIG. 7 shown without the tip element;

FIG. 10 is an isometric view of the inserter of FIG. 7 coupled to the patient-specific acetabular guide of FIG. 1 according to the present teachings;

Corresponding reference numerals indicate corresponding parts throughout the several views of the drawings.

DETAILED DESCRIPTION

Figure 1A:
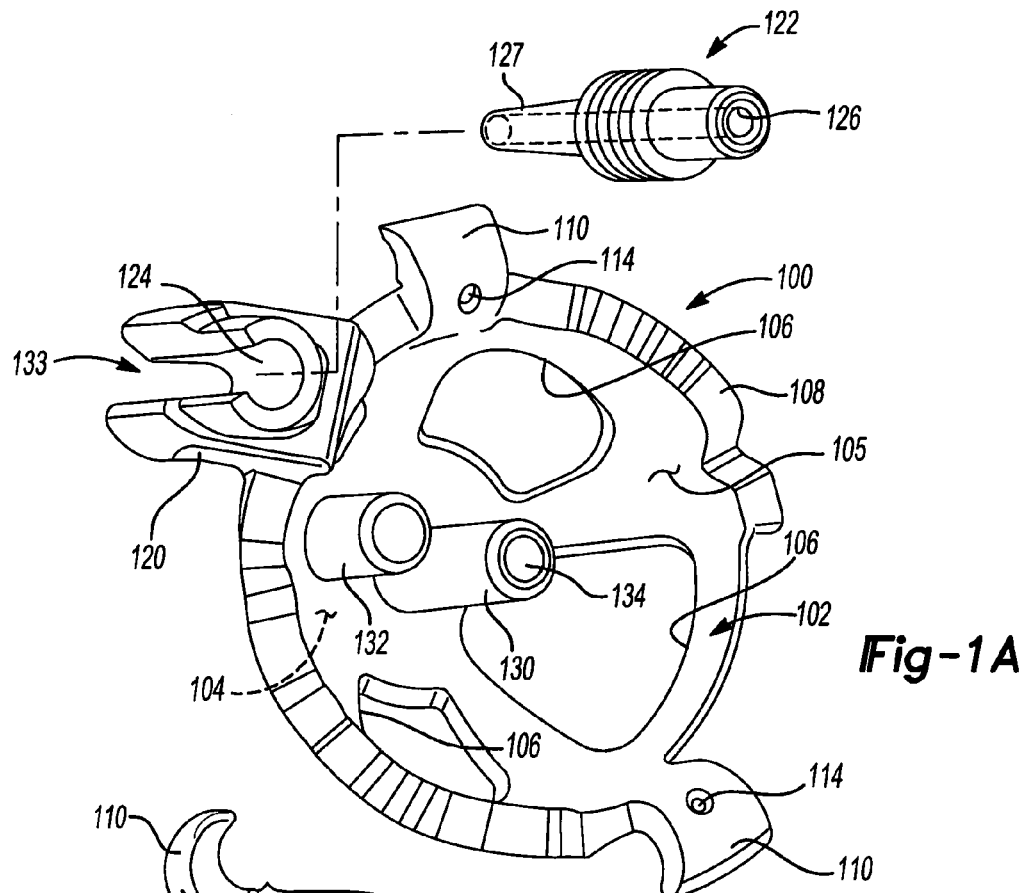
FIG. 1A is a front isometric view of a patient-specific acetabular guide according to the present teachings.
Figure 1B:
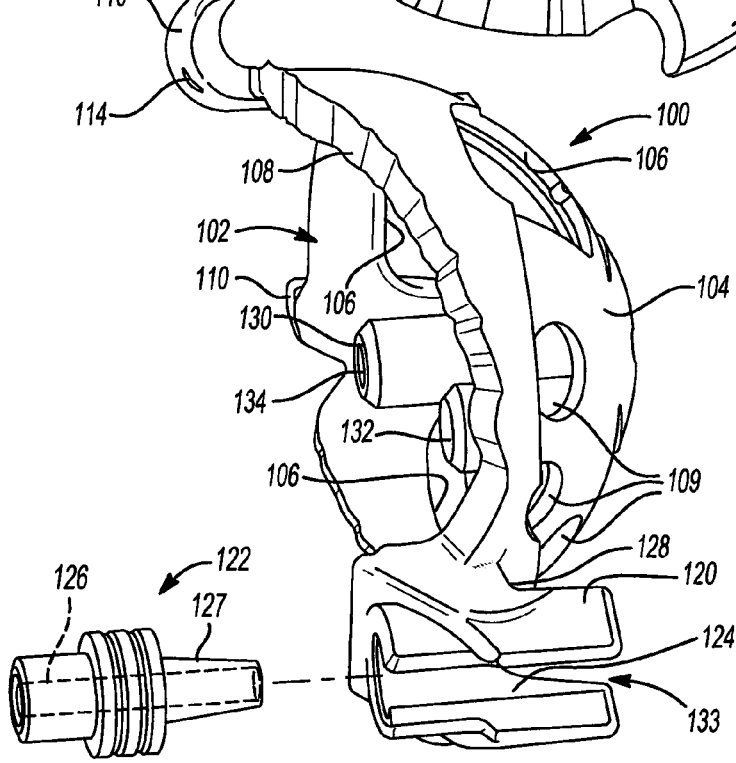
FIG. 1B is a back isometric view patient-specific acetabular guide of FIG. 1A
Figure 2A:
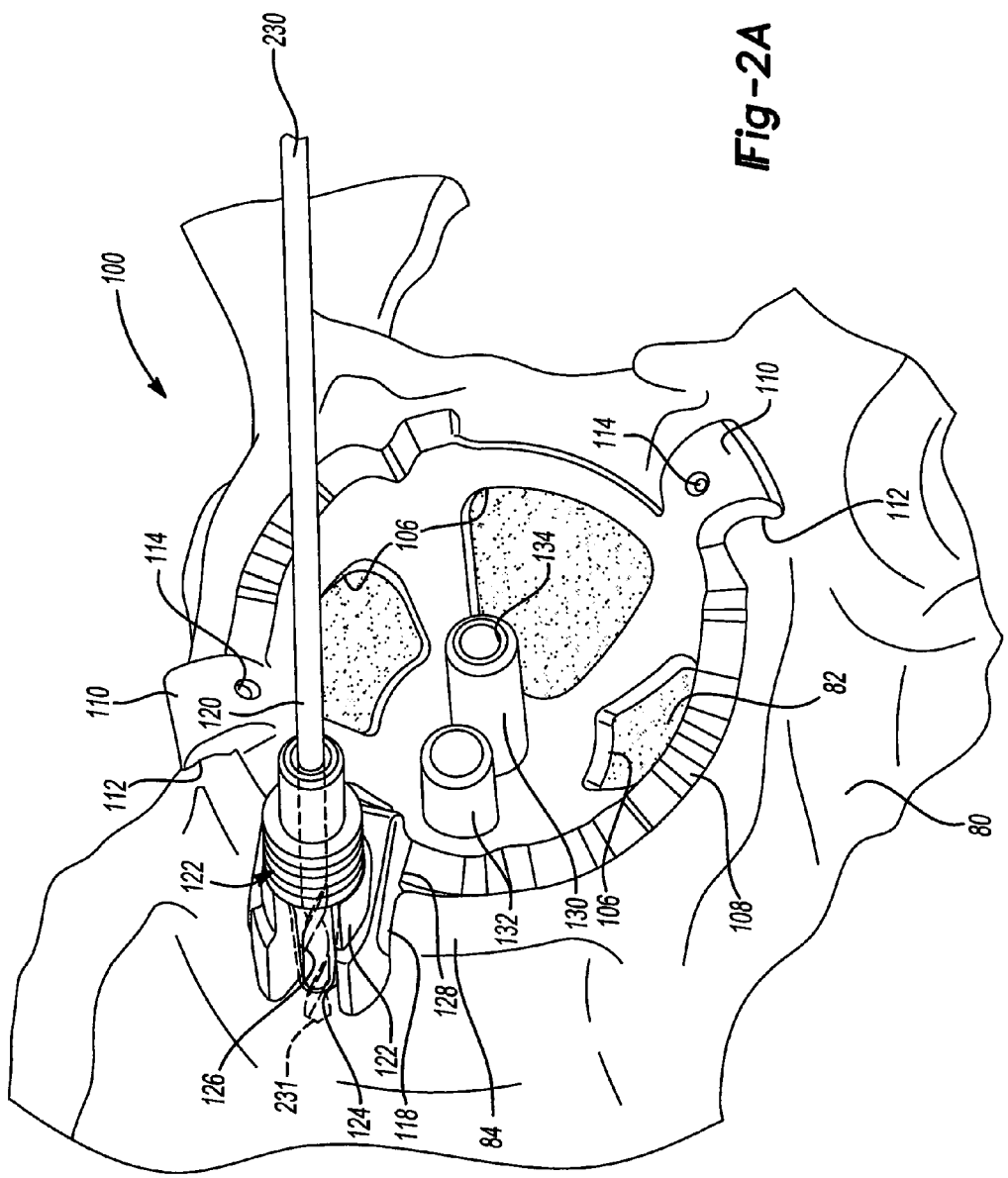
FIG. 2A is an isometric environmental view of the patient-specific acetabular guide of FIG. 1.
Figure 2B:
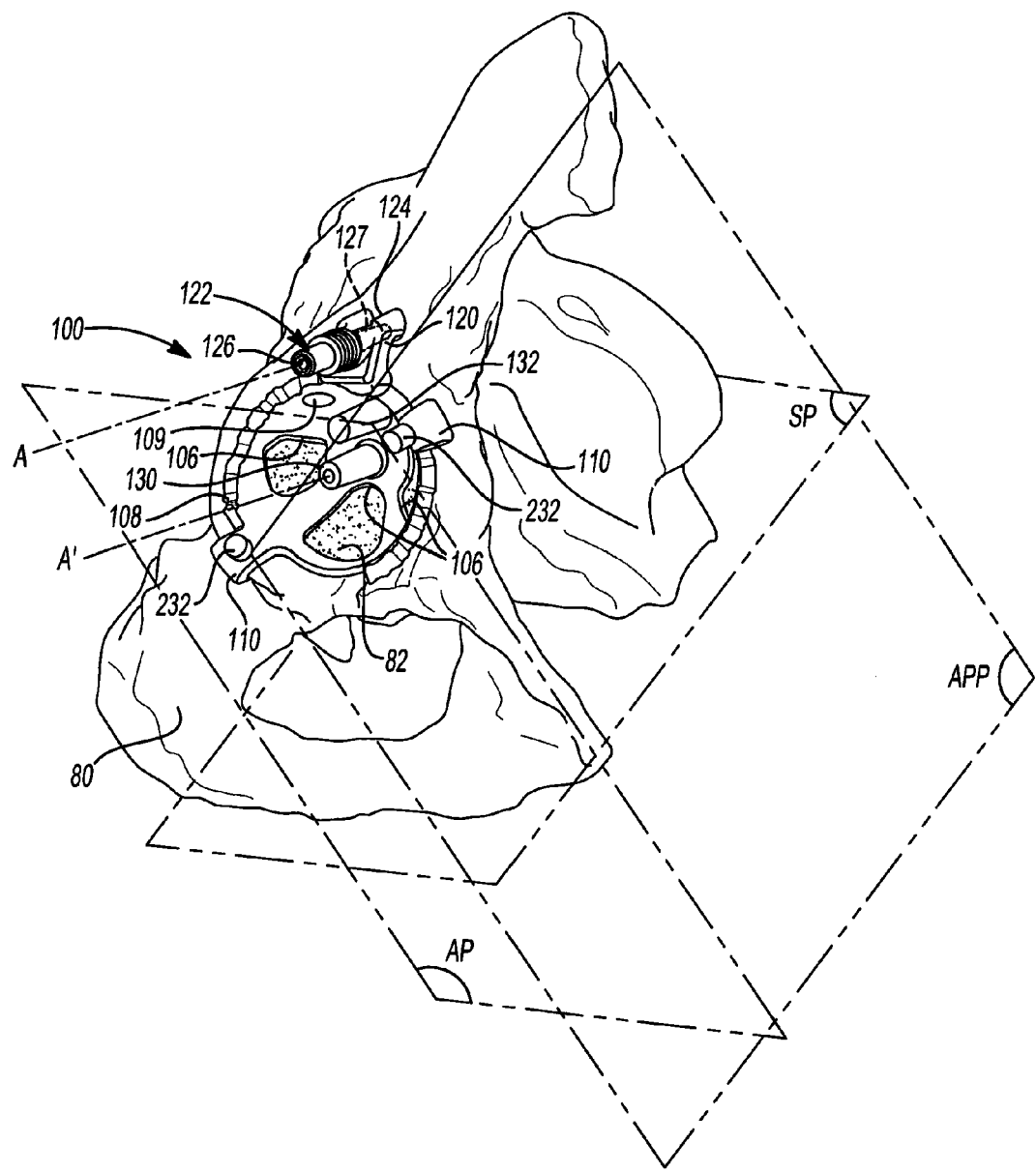
FIG. 2B is another isometric environmental view of the patient-specific acetabular guide of FIG. 1 shown the axial plane, the sagittal and anterior pelvic plane.

The following description is merely exemplary in nature and is in no way intended to limit the present teachings, applications, or uses.

The present teachings generally provide patient-specific acetabular alignment guides, inserters and/or other associated instruments for use in orthopedic surgery, such as, for example, in joint replacement or revision surgery for the hip. The patient-specific alignment guides and associated instruments can be used either with conventional or with patient-specific implant components prepared with computer-assisted imaging methods based on medical scan of the specific patient.

As described in commonly assigned U.S. Pat. No. 8,092,465, issued Jan. 1, 2012, and co-pending U.S. patent application Ser. No. 13/400,652, filed Feb. 21, 2012, both of which are incorporated by reference herein, during a preoperative planning stage, imaging data of the relevant anatomy of a patient can be obtained at a medical facility or doctor's office. The imaging data can include, for example, a detailed scan of a pelvis, hip, knee, ankle or other joint or relevant portion of the patient's anatomy. The imaging data can be obtained using an MRI, CT, and X-Ray, ultrasound or any other imaging systems. The imaging data obtained can be used to construct a three-dimensional computer image of the joint or other portion of the anatomy of the patient and prepare an initial preoperative plan that can include bone or joint preparation, such as planning for resections, milling, reaming, broaching, as well as implant selection and fitting, design of patient-specific guides, templates, tools and alignment protocols for the surgical procedure. Additionally, physical modes of the patient's joint and associated bones can be prepared for visualization and trialing of the guides and implants prior to the surgical procedure.

Computer modeling for obtaining three-dimensional computer images of the relevant patient's anatomy can be provided by various CAD programs, applications and/or software commercially available from various vendors or developers, such as, for example, from by Object Research Systems or ORS, Montreal, Canada. The computer modeling program or other application can be configured and used to plan a preoperative surgical plan, including planning various bone preparation procedures, to select or design/modify implants and design patient-specific guides and tools including patient-specific prosthesis components, and patient-specific tools, including reaming, broaching, milling, drilling or cutting tools, alignment guides, templates and other patient-specific instruments.

The preoperative plan can be stored in any computer storage medium, in a computer file form or any other computer or digital representation, including three-dimensional graphical files or digital data sets. The preoperative plan, in a digital form associated with interactive software or other application, can be made available via a hard medium, a web-based or mobile or cloud service, or a cellular portable device to the surgeon or other medical practitioner, for review. Using the interactive software or application, the surgeon can review the plan, and manipulate the position of images of various implant components relative to an image of the anatomy. The surgeon can modify the plan and send it to the manufacturer with recommendations or changes. The interactive review process can be repeated until a final, approved plan, is sent to a manufacturing facility for preparing the actual physical components. In other embodiments, physical and digital patient-specific bone models guides and instruments and can be provided preoperatively to the surgeon for trialing and marking.

After the surgical plan is approved by the surgeon, patient-specific implants and associated tools, including, for example, alignment guides, cutting/milling/reaming/broaching or other tools for the surgical preparation of the joint or other anatomy portion of the specific patient can be designed using a CAD program or other three-dimensional modeling software, such as the software provided by Object Research Systems or ORS, Montreal, Canada, for example, according to the preoperative surgical plan. Patient-specific guides and other instruments can be manufactured by various stereolithography methods, selective laser sintering, fused deposition modeling or other rapid prototyping methods. In some embodiments, computer instructions of tool paths for machining the patient-specific guides and/or implants can be generated and stored in a tool path data file. The tool path data can be provided as input to a CNC mill or other automated machining system, and the tools and implants can be machined from polymer, ceramic, metal or other suitable material depending on the use, and sterilized. The sterilized tools and implants can be shipped to the surgeon or medical facility for use during the surgical procedure.

Patient-specific implants, guides, templates, tools or portions thereof are defined herein as those constructed by a preoperative plan for a specific patient from three-dimensional images of the specific patient's anatomy reconstructed from preoperative medical scans of the patient. The patient-specific components are constructed to closely conform and mate or match substantially as a negative mold or negative surface or inverse or mirror surface of corresponding surface portions of the patient's anatomy, including bone surfaces with or without associated soft tissue, such as articular cartilage, for example, depending on the particular procedure, implant and tool use. Minute irregularities of the patient's joint surfaces need not be mirrored.

As discussed above, patient-specific alignment guides and implants are generally configured to match the anatomy of a specific patient and can fit in only one position on a corresponding surface of the specific patient because anatomic features that are unique to each patient can function as landmarks and can guide placement of the alignment guide or implant in only one position without the need of intraoperative navigation, patient marking or other intraoperative guidance. The patient-specific alignment guides are generally configured and manufactured using computer modeling based on the patient's 3-D anatomic image and have an engagement surface that is made to conformingly contact and match as a mirror or negative or inverse surface to a corresponding surface of a three-dimensional image/model of the patient's bone surface (with or without cartilage or other soft tissue), by the computer methods discussed above. Generally, the patient specific guide has an exterior surface that contacts about 80% of the patient's anatomy when properly positioned, including about 90%, and about 98%. The exterior surface of the patient matched guide can, therefore, substantially mate with the selected portion of the anatomy. It is understood, however, that certain exterior portions of a patient specific guide may not have substantial contact with the patient, while other portions are designed to ensure contact even when other portions are not contacting the patient. Thus, a patient matched guide can have portions that are substantially patient matched and have or can achieve the selected amount of contact with the patient.

The patient-specific alignment guides can include one or more custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan. The patient-specific alignment guides can be used in minimally invasive surgery, and also in surgery with multiple minimally-invasive incisions. Various alignment guides and pre-operative planning procedures are disclosed in commonly assigned U.S. Pat. No. 8,092,465, issued Jan. 10, 2012; U.S. Pat. No. 8,070,752, issued Dec. 6, 2011; U.S. Pat. No. 8,133,234, issued Mar. 13, 2012; co-pending U.S. patent application Ser. No. 12/211407, filed Sep. 16, 2008; co-pending U.S. patent application Ser. No. 12/025414, filed Feb. 4, 2008; co-pending 13/111007, filed May 19, 2011; co-pending U.S. patent application Ser. No. 13/041469, filed Mar. 7, 2011; and co-pending U.S. patent application Ser. No. 13/400652, filed Feb. 21, 2012. The disclosures of the above patents and applications are incorporated herein by reference.

Referring to FIGS. 1A-9, the present teachings provide a patient-specific acetabular guide 100 and an acetabular guide inserter 300 an adapter element 350. As discussed herein, the adapter element may or may not be removable from a handle portion during operation. The acetabular guide 100 can be used in connection with various other instruments to generally provide a patient-specific alignment axis A. The patient-specific alignment axis A is used to insert an alignment pin 230 and generally to orient, insert, and implant an acetabular implant or acetabular cup 250 in an acetabulum (or acetabulum cavity) 82 of the patient, to facilitate guided reaming of the acetabulum 82, and generally guide any instruments and procedures relative to the alignment axis A or the alignment pin 230. The alignment axis A is determined during the preoperative plan from the three-dimensional image of the hip joint of the patient as the axis along which the acetabular implant 250 is to be centered and inserted. The alignment axis A is generally perpendicular the acetabulum 82 and corresponding acetabular engagement surface 252 of the acetabular implant 250. More specifically, with reference to FIG. 2B, the orientation (i.e., angles) of the alignment axis A can be selected and specified relative the axial plane (AP), sagittal plane (SP) and anterior pelvic plane (APP). The coronal plane is a vertical plane that is orthogonal to the axial and sagittal planes (not shown). The anterior pelvic plane (APP) is defined as a plane passing through the two anterior iliac spines and the pubic symphysis of the pelvis 80 of the patient. The APP may deviate from being parallel to the coronal plane when viewed in the weight-bearing profile of the patient (standing). Additionally, the APP plane may have a different orientation in the supine position. The deviation varies from patient to patient, such that the anterior pelvic plane cannot be relied on by the surgeon without additional information to guide the acetabular implant and avoid impingement during motion. The angle between the anterior pelvic plane and the coronal plane can be referenced as a pelvic tilt and is zero when the anterior pelvic plane is parallel to the coronal plane. The present teachings determine a patient-specific axis for inserting an acetabular implant. The patient-specific alignment axis is physically and uniquely identified by the orientation of an alignment pin inserted into the bone using the patient-specific acetabular guide and landmark registration incorporated into the acetabular guide during the preoperative plan. Specifically, the preoperative plan that is based on images of the hip joint of the patient can accurately determine the orientation of the alignment axis A and fix it intraoperatively via the patient-specific acetabular guide 100 on the pelvis 80 of the patient to guide the surgeon during the surgical procedure.

The patient-specific acetabular guide 100 can engage the acetabulum 82 of the specific patient in a unique (only one) position and can provide an accurate alignment axis A relative to the planned orientation of the acetabular implant 250. The patient-specific acetabular guide 100 can also provide secure fitting and rotational stability in a design that is lightweight and has compact size and small bulk.

FIGS. 1A-3 illustrate a patient-specific acetabular guide 100 that has a dome-shaped body 102 with a three dimensional patient-specific undersurface or outer surface 104 configured to contact and engage the acetabulum 82. The outer surface 104 is designed and/or formed to match as a negative of a corresponding surface of the acetabulum 82 from the three-dimensional image of the patient's hip joint. Thus, the outer surface 104 is formed to mate closely, such as to contact about 85% to about 100% of the acetabulum 82 when positioned in the acetabulum 82.

The dome-shaped body 102 of the patient-specific acetabular guide 100 can have one or more openings in the form of windows 106 that reduce the weight of the patient-specific acetabular guide 100 and provide improved visualization of the underlying anatomy. The dome-shaped body 102 can also include additional holes or other apertures 109 for drilling holes in the acetabulum 82 and corresponding to holes 254 for fixation screws of the acetabular implant 250. The dome-shaped body 102 of the patient-specific acetabular guide 100 is bounded by a guide rim 108 in the form of a closed-contour peripheral annular surface that has an uneven, irregular, jagged or wavy shape that follows the corresponding irregular shape of an acetabular rim 84 (and periacetabular surface) around the acetabulum 82 of the patient. Additionally, the patient-specific acetabular guide 100 can include one or more registration hooks or extensions 110 that extend from the guide rim 108 along a three-dimensional curved surface around the acetabular rim 84 at different and spaced-apart positions. The registration hooks 110 are configured to provide additional registration locations for the patient-specific acetabular guide 100 by replicating corresponding underlying surface portions or landmarks of the acetabular rim 84 in a patient-specific manner. Specifically, each registration hook 110 can have a curved (three-dimensional) undersurface 112 that is patient-specific and negative of the surface of the acetabular rim 84 at specific locations selected as landmark locations during the preoperative plan for the patient. Each registration hook 110 can include a hole 114 for receiving a fixation pin or other fixation element 116 (shown in FIG. 4) for attaching the patient-specific acetabular guide 100 to the pelvis of the patient.

The patient-specific acetabular guide 100 can include a removable or non-removable registration and alignment guide 120 (referenced as registration guide 120, for short) that has a longitudinal bore 124 along the patient-specific alignment orientation A. A removable drill insert 122 with a longitudinal bore 126 can be received concentrically in the bore 124 of the registration guide 120. The wall of the bore 124 of the registration guide 120 can define a taper that engages a complementary taper 127 of an end of the removable drill insert 122. The complementary tapers can ensure appropriate and selected alignment of the bore 124 and the insert bore 126. Thus, the bore 124 and the insert bore 126 can be concentric and coextensive.

The drill insert 122 can provide stability during the insertion of an alignment pin 230 that can define the alignment axis A. The alignment pin 230 can include a drill tip 231 that can drill into the bone of or near the acetabulum. The alignment pin 230 is received into the concentric and coextensive bores 124, 126 of the registration guide 120 and of the drill insert 122. Accordingly, the alignment pin 230 is oriented along the alignment axis A. The drill insert 122 can be formed of a tough and/or strong material. For example, the drill insert 122 can be metallic and reusable, while the registration guide 120 and the acetabular guide 100 are patient-specific and can be made of a softer material, such as a polymer material, and can be disposable. The tough material of the drill insert 122 can engage the alignment pin 230 without deformation and protect the registration guide 120 from damage due to engaging the alignment pin 230.

The registration guide 120 has an undersurface portion that is a patient-specific undersurface 128 that can hook around or snap-on or otherwise engage and contact the guide rim 108 at a pre-defined marked location determined during the preoperative plan of the patient. The registration guide 120 that includes the patient-specific undersurface 128 matches the surface of the acetabular rim 84 and/or periacetabular area of the pelvis 80 of the patient at a corresponding location. The bore 124 of the registration guide 120 and the bore 126 of the drill insert 122 can have an open (i.e., non-continuous) periphery defining a longitudinal slit 133 that is configured to allow the patient-specific acetabular guide 100 to be removed from the pelvis of the patient without removing the alignment pin 230 that is inserted into the pelvis 80 and defines the alignment axis A. In other words, the patient-specific acetabular guide 100 can be also removed by side or lateral motion relative to the slit 133 and the longitudinal axis A and not necessarily by only motion along the alignment axis A or along the alignment pin 230.

The patient-specific acetabular guide 100 can include first and second posts 130, 132 extending from an interior surface 105 (opposite to outer surface 104) of the dome-shaped body 102 of the patient-specific acetabular guide 100. The first post 130 can be tubular and can define a bore 134 that passes through the dome-shaped body 102 of the acetabular guide for optional fixation to the acetabulum 82 using a pin or other fastener. The bore 134 is not necessary, however, and the post 130 can be a closed hollow post or a solid post. The first post 130 can be centrally located and perpendicular relative to the dome-shaped body 102 of the patient-specific acetabular guide 100 and the underlying surface of the acetabulum 82. The second post 132 can be offset relative to the first post 130 along a radial direction relative to the periphery of the guide rim 108. The second post 132 can be shorter in height relative to the first post 130. The posts 130, 132 can be used to insert the patient-specific acetabular guide 100 using an acetabular guide inserter, such as the acetabular guide inserter 300 shown in FIG. 8.

It should be noted that other inserters can also be used to connect to one or both posts 130, 132 and be coupled to the patient-specific acetabular guide 100. According to various embodiments, the acetabular guide inserter 300 can be modular and include an elongated portion 302 and the adapter element (or inserter tip) 350 can be removable from the elongated portion 302. The elongated portion 302 can include a handle portion 308 and a shaft 304 having a distal post or boss 306. The adapter element 350 includes a tubular post 352 with a first bore 354 configured to connect and receive the boss 306 of the elongated portion 302 of the acetabular guide inserter 300. The elongated portion 302 can be interconnected to the adapter 350 at an appropriate time to insert the guide 100 (e.g. after the adapter 350 has engaged the post 130). It is understood, however, that the adapter can be manufactured to be fixed to the elongated portion 302 for use. For example, the elongated portion 302 and the adapter 350 can be formed as one piece or fixed together, such as with welding or an adhesive. Accordingly, it is understood that the inserter 300 need not be separable for use by a user.

Figure 3:
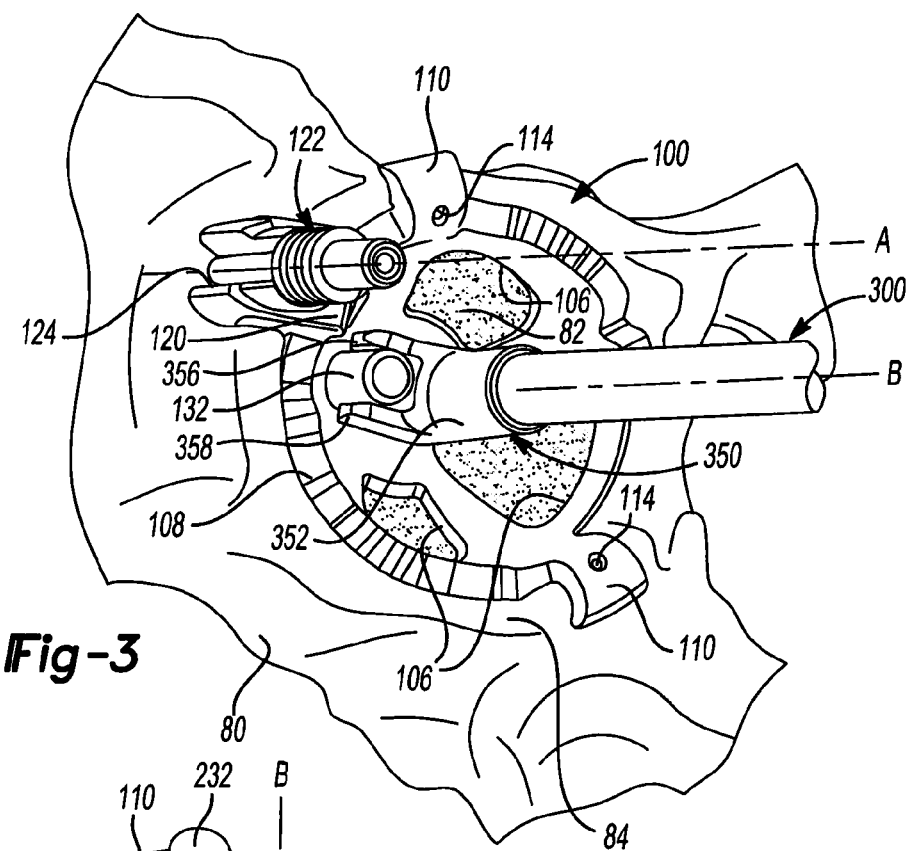
FIG. 3 is an isometric environmental view of the patient-specific acetabular guide of FIG. 1 shown with a tip element of an acetabular guide inserter according to the present teachings.
Figure 4:
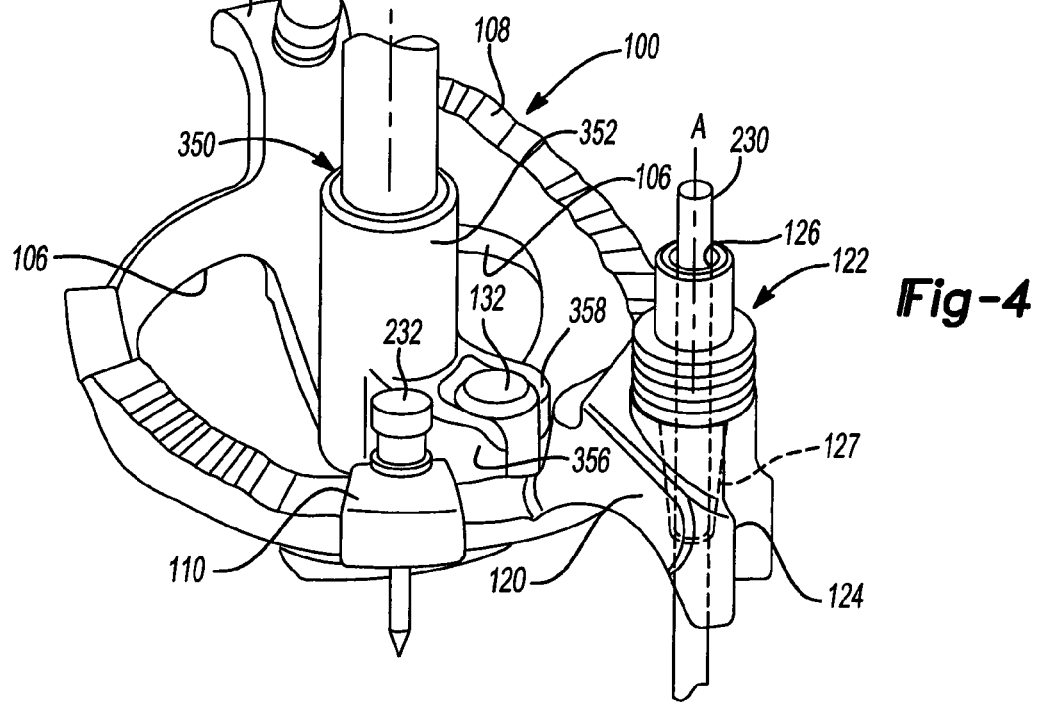
FIG. 4 is an isometric view of the patient-specific acetabular guide of FIG. 1 shown with the tip element of FIG. 3.
Figure 5:
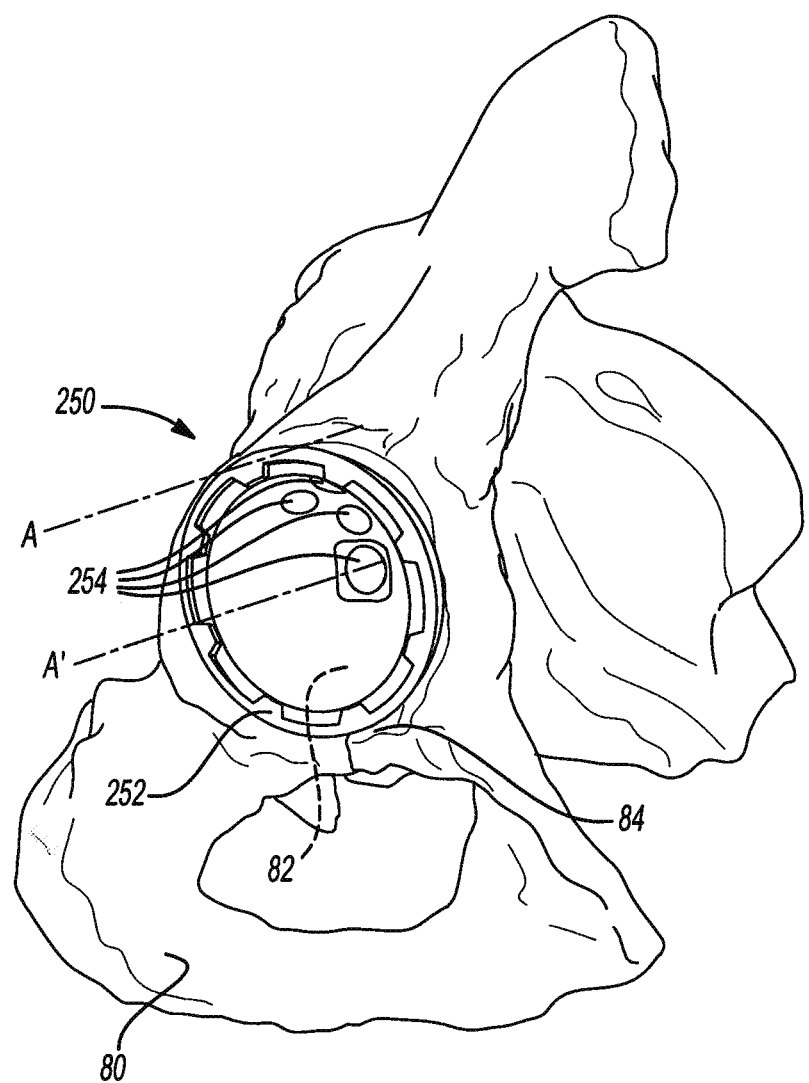
FIG. 5 is an isometric environmental view of an acetabular implant.
Figure 6:
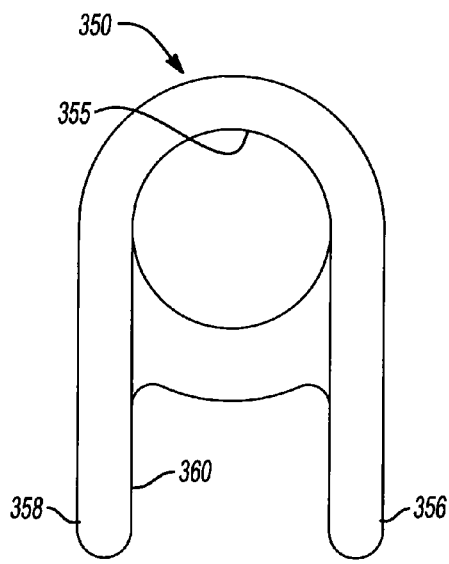
FIG. 6 is a bottom view of the instrument handle tip element shown in FIG. 4.
Figure 7:
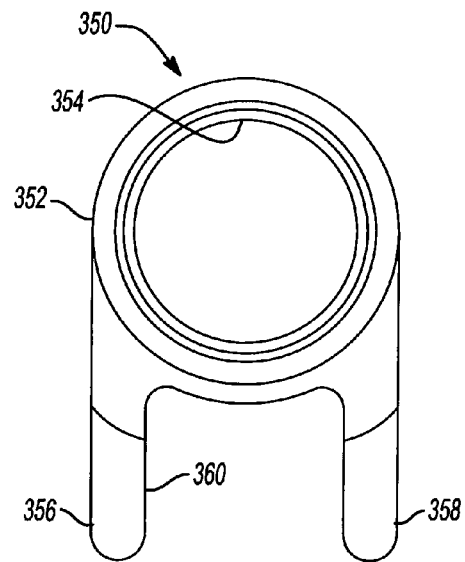
FIG. 7 is a top view of the instrument handle tip element shown in FIG. 4.
Figure 8:
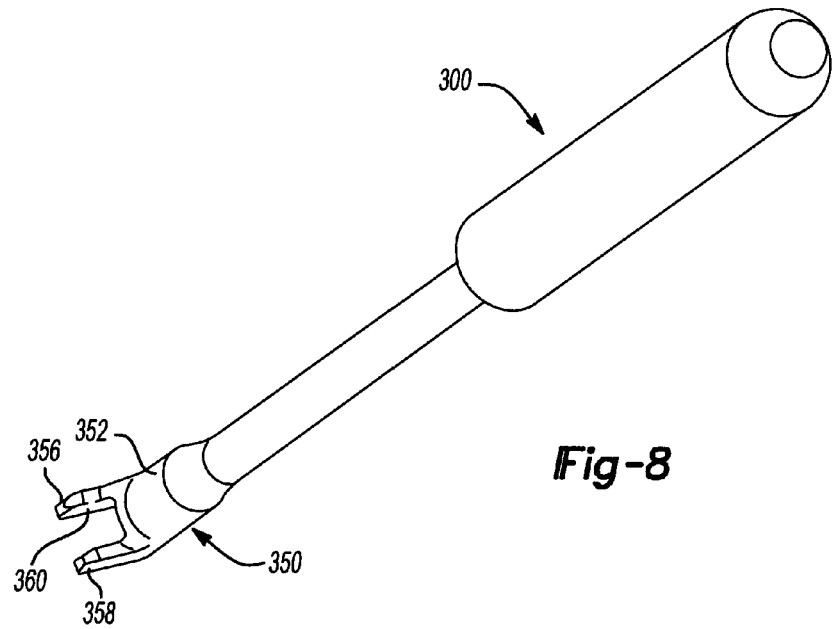
FIG. 8 is an isometric view of an acetabular guide inserter shown with the tip element of FIG. 6.
Figure 11:
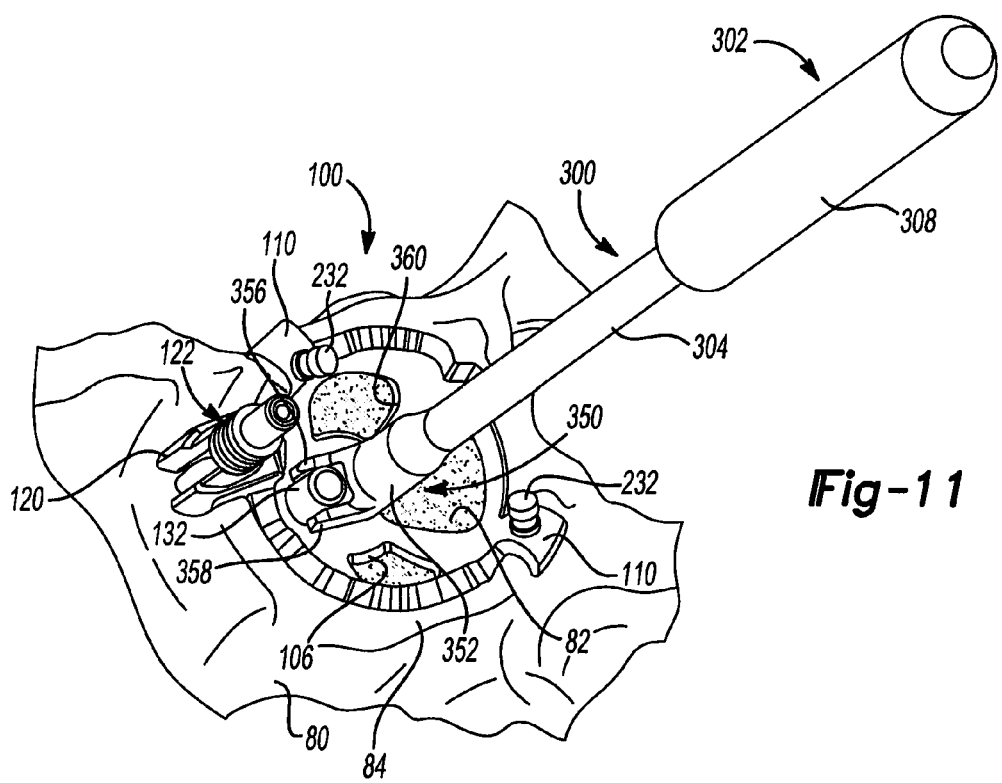
FIG. 11 is an environment isometric view of the inserter of FIG. 7 coupled to the patient-specific acetabular guide of FIG. 1 according to the present teachings.
Figure 12:
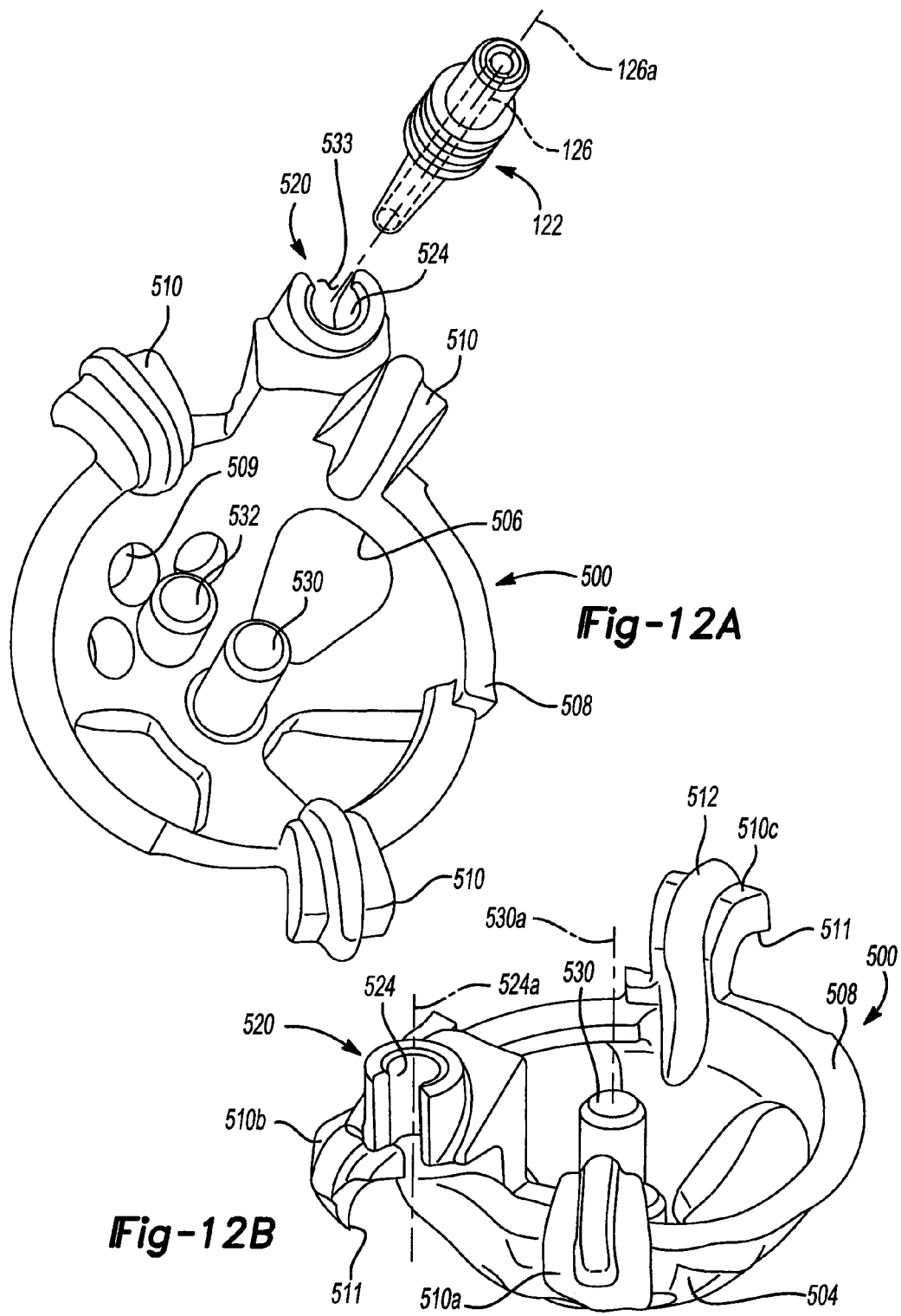
FIGS. 12A and 12B illustrate top isometric views of a patient-specific acetabular guide according to the present teachings.

The adapter element 350 includes a second bore 355 opposite to the first bore 354 and configured to receive the first tubular post 130 of the acetabular guide 100. The adapter element 350 includes first and second arms or flanges 356, 358 extending from a distal end of the adapter element 350 opposite to the post 352 and around the second bore 355. The first and second flanges 356, 358 define an open channel or a U-shaped inner surface 360 that can receive and hold the second post 132. The first and second flanges 356, 358 can be resiliently coupled to adapter element 350 and can be configured to snap-on to the second post 132 of the patient-specific acetabular guide 100 while the first post 130 of the acetabular guide 100 is received in the second bore 355 of the adapter element 350, as shown in FIGS. 3, 4 and 10.

The patient-specific acetabular guide 100 can be inserted in the acetabulum 82 using the inserter 300, as shown in FIG. 9. The inserter 300 can be removed, and the patient-specific acetabular guide 100 can be stabilized to the bone with fixation pins 232. A hole can be drilled through the drill insert 122 into the bone and the alignment pin 230 can be inserted along the alignment axis A defined by the registration guide 120. It is understood, that inserting the alignment pin 230 need not be a two-step process. For example, the alignment pin 230 can include a drill tip or portion 231 such that the alignment pin 230 is directly drilled into the bone.

Other holes can also be drilled into the bone through the holes 109 of the patient-specific acetabular guide 100 for attaching the acetabular implant 250. The fixation pins 232 can be removed and then the patient-specific acetabular guide 100 can be removed sideways without removing the alignment pin 230 and without disturbing its orientation along the alignment axis A. The acetabular implant 250 can be inserted in the acetabulum along an axis A' parallel to the alignment axis A defined by the alignment pin 230 that is still attached to the bone. Additionally, reaming or other acetabular bone preparations can be performed using the orientation defined by the alignment pin 230 prior to the insertion of the acetabular implant 250.

The patient-specific acetabular guide 100 does not require the use of additional secondary guides to provide an alignment orientation for inserting an acetabular implant 250 or guiding other instruments. As such, the patient-specific acetabular guide 100 can be conveniently used in hip arthroplasty with an anterior supine incision along a patient-specific alignment axis A. The alignment axis A is preoperatively determined and transferred to the pelvis 80 using an alignment pin 230 guided by the registration guide 120 of the patient-specific acetabular guide 100, as discussed above.

According to various embodiments, an acetabular guide 500 is illustrated in FIGS. 12A-14. The acetabular guide 500 can be similar to the acetabular guide 100, discussed above, including variations discussed further herein. Nevertheless, the acetabular guide 500 can be inserted or positioned in the acetabulum 82 of the pelvis 80, in a manner similar to that of the acetabular guide 100.

The acetabular guide 500 can be positioned to allow for guiding placement of the alignment pin 230 at a selected location in the pelvis 80, as discussed further herein. The alignment pin 230 can be positioned to illustrate or identify a predetermined alignment axis A, as discussed above. The alignment pin 230 can be positioned through the removable drill insert 122 that is positioned in a removable or non-removable registration or alignment guide 520. The acetabular guide 500 can include portions that are substantially similar to portions of the alignment guide 100, and will not be described in detail here. The acetabular guide 500 can include an outer dome surface 504 that can be positioned to engage the acetabulum 82 in a manner similar to the outer dome surface 104 of the acetabular guide 100, as discussed above. Accordingly, the outer dome surface 504 and/or an upper rim 508 can include a geometrical configuration that are substantially similar or mirror the acetabulum or the rim of the acetabulum 82. For example, the mirror surface or patient matched surface can contact any selected amount of the acetabulum, such as greater than about 80%, including about 80%-90%, including further at least about 98%. Accordingly, the acetabular guide 520 can be substantially patient matched. The determination or geometry of the acetabular guide 500 can be based on various techniques, including image data obtained of the patient in a process as discussed above. The dome surface 504 and other portions of the guide 500 can be designed to be patient matched for engaging the patient in substantially only one orientation and location.

The acetabular guide 500 can further include various portions that engage an upper rim or edge or a portion external to the acetabulum 82. For example, the acetabular guide 500 can include one or more registration hooks 510. The registration hooks 510 can include a geometry or structure that extends from the upper rim 508, in one or more dimensions, to have an external engaging or contacting finger portion 511. The geometry of the registration hook 510 can further include a reinforcing rib portion 512 that extends at least a portion of a length of the registration hook 510 to assist in providing rigidity and/or geometrical stability to the registration hooks 510.

The registration hooks 510 can be positioned at various positions around the rim 508 of the registration guide 500. However, it is understood, that various registration hooks are not required and may be selected to be removed or not provided with the acetabular guide 500. For example, a registration hook that is positioned or would be positioned near an ischium of the pelvis 80, such as an ischial registration hook 510c, need not be required. According to various embodiments, therefore, for example, for efficiency of manufacturing, the ischial registration hook 510c may not be provided. Nevertheless, the registration hooks 510a and 510b can be provided to assist in providing additional registration locations relative to the acetabular guide 500. Generally, the dome 504 of the acetabular guide 500 can provide appropriate registration of the acetabular guide 500 relative to the acetabulum 82 of the patient. As discussed herein, the registration of the hooks 510 and/or the dome 504 can ensure that the guide 500 is located and oriented at a pre-selected location and orientation relative to the pelvis 80 of the specific patient.

The acetabular guide 500 can also be positioned and held in place relative to the patient and the acetabulum 82 based upon the geometry of the dome 504 and/or the registration hooks 510a and/or 510b. Accordingly, additional fixation mechanisms, such as pins positioned through holes in the registration hooks 510 need not be provided. It is understood, however, that additional fixation mechanisms, such as pins positioned through the registration hooks 510, can be provided. Also, additional fixation holes 509 can be formed through the dome 504 to receive fixation pins or screws into the acetabulum 82.

Additionally, the alignment or registration guide 520 can be formed and positioned to be integral or connected to at least one of the registration hooks 510b. The positioning of the alignment guide 520 relative to the registration hook 510b is not required, but the combination can assist in providing rigidity and strength to each of the alignment guide 520 and the registration hook 510b. Additionally, the position of the registration hook 510b can be aligned with or positioned relative to the alignment guide 520 due to a positioning or selected positioning of the alignment pin 230 relative to the acetabulum 82. As discussed herein, the pin 230 is positioned through an alignment bore 524 formed through the alignment guide 520.

The acetabular guide 500 can be positioned within the acetabulum 82 in a manner substantially similar to the acetabular guide 100, discussed above, as exemplarily illustrated in FIGS. 13 and 14. The acetabular guide 500 can be positioned with the inserter 300, as discussed above. The inserter can engage a first post 530, such as with a central bore or blind bore formed in the inserter 300. The inserter 300 can further include one or more fingers or flanges 356 and 358, as discussed above, to engage a second or additional post 532. The acetabular guide 500, therefore, can be positioned within the acetabulum 82 of the patient substantially as discussed above, and as illustrated in FIGS. 3 and 4. The posts 530 and 532, however, can be closed and need not include any passages or fixation portions to assist in holding the acetabular guide 500 relative to the acetabulum 82. It is understood that other passages, such as the passage 509, can be formed through the guide 500 to allow for positioning of various fixation portions through the acetabular guide 500.

Additionally, viewing passages 506 can be formed through the guide 500 to assist in viewing the acetabulum 82 of the patient. The viewing passages 506 can allow a user to view the acetabulum 82 during and after placement of the guide 500. This can assist in ensuring that the acetabular guide 500 is positioned within the patient in the acetabulum 82 in a selected manner.

Figure 14:
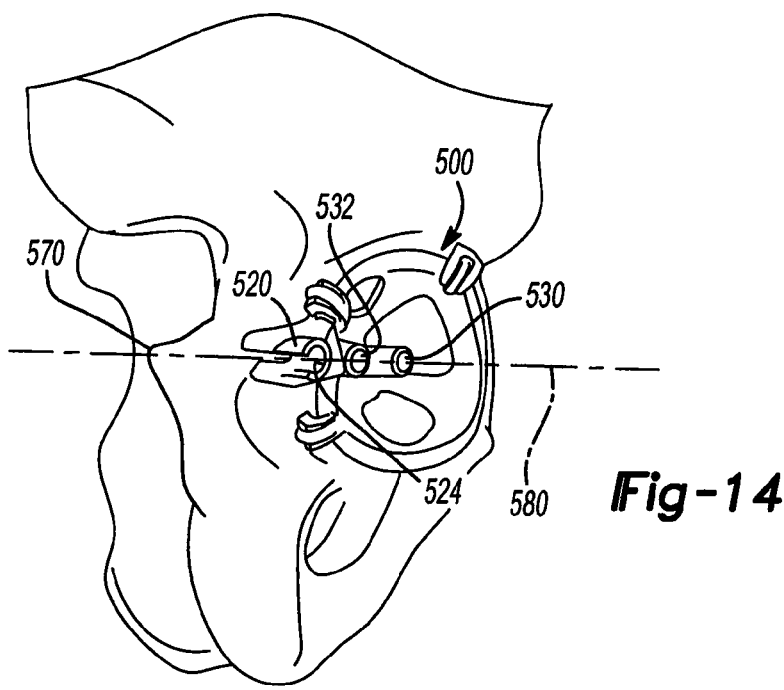
FIG. 14 illustrates a lesser detail isometric environmental view of the patient-specific acetabular guide of FIG. 12A.

The acetabular guide 500 is positioned within the acetabulum 82 such that the alignment guide 520 is selectively positioned relative to the inferior ischial spine. In particular, when the drill guide 122 is positioned within the alignment bore 524, then the alignment pin 230 that is passed through the drill guide 122 is on a line 580 that extends through the central post 530 and the interior spine of the ischium 570, as illustrated in FIG. 14. The guide pin 230 is also placed exterior to the acetabulum 83.

Figure 13:
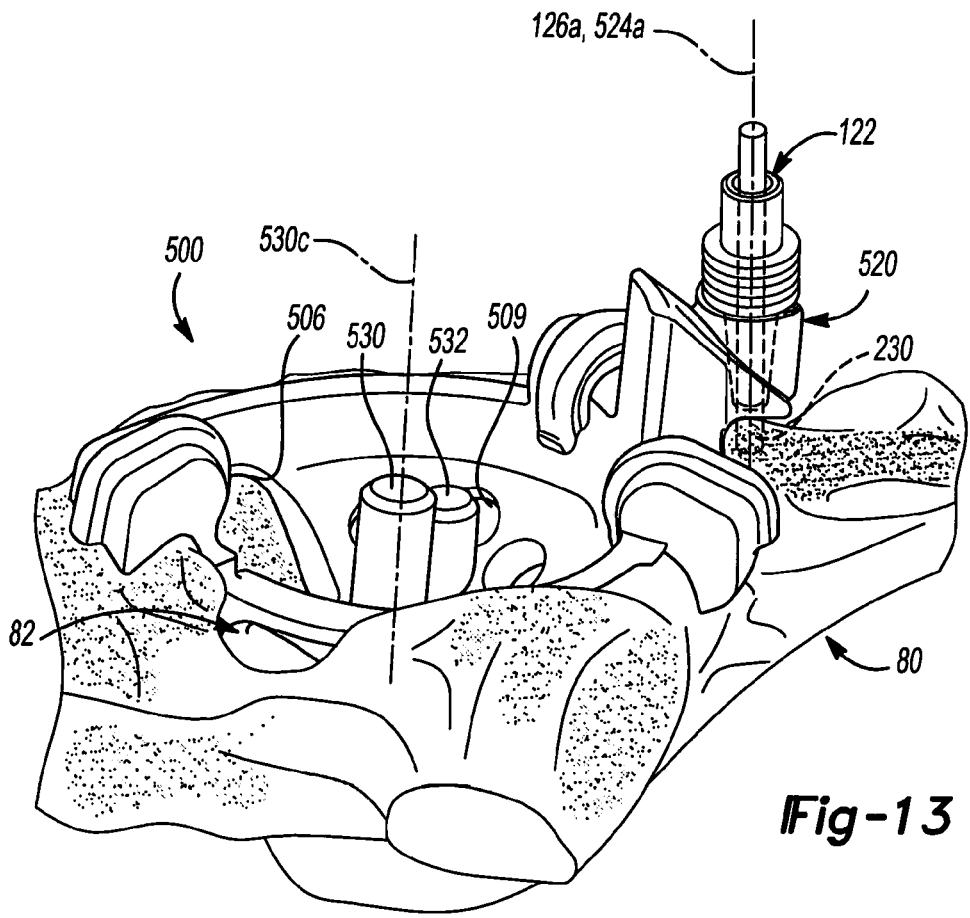
FIG. 13 illustrates a detail isometric environmental view of the patient-specific acetabular guide of FIG. 12A.

With continued reference to FIGS. 13 and 14, the line 580 is defined through the interior spine 570, the guide bore 524, and the central post 530 of the acetabular guide 500. According to various embodiments, the guide 520 and/or the guide bore 524 define a guide long axis 524a. The central post 530 defines a post long axis 530a. The drill guide 122 also defines the insert bore 126, and the drill guide 122 and/or the insert bore 126 defines an insert long axis 126a. The respective long axes are of the various portions. The guide line 580 can be at least partially defined as a line through at least the post long axis 530a and one of the guide long axis 524a or the insert long axis 126a. The guide line 580 then extends to intersect the inferior ischial spine 570.

As discussed above, the shape and geometry of the acetabular guide 500 can be formed such that the acetabular guide 500 engages the acetabulum 82 in a manner such that the seating or engaging of the acetabular guide 500 is achieved when the alignment bore 524 is aligned along the line 580. Thus, the guide 500 is designed and manufactured to register with the acetabulum 82 of the specific patient in a single location and orientation. The design of the guide 500 can be based on images of the patient, as discussed above.

The single orientation and location of the guide 500 is generally relative to the inferior ischial spine 570. The guide line 580 is designed and selected to pass through the inferior ischial spine 570, as illustrated in FIG. 14. The one or more images acquired of the patient allows for determining of a geometry for designing and manufacturing the guide 500, such as the dome 504 and/or registration hooks 510, to properly engage the acetabulum 82 of the patient such that the alignment bore 524 is positioned on the line 580.

As discussed above, the insertion device 300 can be used to position the acetabular guide 500 within the acetabulum 82 to achieve the alignment of the alignment bore 524 with the spine 570 along the line 580. The drill guide insert 122 can be positioned within the guide bore 524 in a selected manner, such as that discussed above. For example, the drill guide 122 can include an external taper then engages an internal taper of the alignment bore 524 to ensure a substantially aligned fit of the drill guide 122. The alignment pin 230 can then be drilled into the pelvis of the patient to position the alignment pin 230 on the line 580.

Accordingly, the acetabular guide 500 can be used to align and guide the alignment pin 230 into the pelvis of the patient to allow for guiding or alignment of various instruments following positioning of the alignment pin 230. For example, a reamer instrument, an insertion instrument for an acetabular shell, and/or other instrument can be provided to align with the alignment pin 230 once it is positioned within the pelvis. As discussed above, the drill guide member 122 can be removed from the alignment bore 524 and moved along the length of the alignment pin 230 to remove it from the patient. The acetabular guide 500 can then be removed from the alignment pin 230, such as through a side opening 533 formed through the alignment guide 520. Therefore, the acetabular guide 500 need not be removed along the length of the alignment pin 230, but can be removed with a sideways or lateral motion.

In positioning the alignment pin 230 on the line 580, the alignment pin 230 can be positioned external to the acetabulum 82. Additionally, the positioning of the alignment pin 230 on the line 580 external to the acetabulum 82 positions the alignment pin 230 in a region of the pelvis 80 that is superior to the acetabulum 82 and posterior to the anterior inferior spine. Generally, the region superior to the acetabulum can provide substantially dense and strong bone of the pelvis for engaging the alignment pin 230. Accordingly, the alignment pin 230 can be firmly held in the pelvis relative to the acetabulum 82 during a procedure. The alignment pin 230 can be positioned within the pelvis of a patient for performing a procedure on the acetabulum and is generally selected to be maintained in a single orientation and location once placed. Accordingly, positioning the alignment pin 230 in substantially dense bone can assist in maintaining the alignment pin 230 in the selected location after the alignment pin 230 is positioned within the pelvis of the patient. Accordingly, the positioning the alignment bore 524 on the line 580 can assist in assuring that the alignment pin 230 will engage a selectively strong and dense bone portion to assure maintaining the selected position and orientation of the alignment pin 230 during the rest of the procedure.

The procedure can then proceed, as discussed above, including reaming the acetabulum 82 by aligning a reamer shaft with the alignment pin 230, placing an acetabular shell within the acetabulum 82 by aligning the inserter shaft with the alignment pin 230, and other procedure portions where the alignment pin 230 provides a reference for a user relative to the pelvis for performing a procedure in the acetabulum. Again, the acetabular guide 500 can be initially positioned within the acetabulum 82 in a substantially precise location and orientation based upon the geometry of the acetabular guide 500, including the external dome 504. The geometry of the acetabular guide 500 can ensure that the acetabular guide 500 engages the patient in substantially single and pre-selected orientation and location to ensure that the alignment bore 524 is positioned relative to the patient in the pre-selected location and orientation. Therefore, the alignment pin 230 that is passed through the alignment bore 524 is at the selected location and orientation generally on the line 580 and external to the acetabulum 82.

Various patient-specific guides, secondary guides, reamers, guide handles, inserters, impactors, support devices, electronic positioners and other instruments can be used in various combinations and based on surgeon preferences or patient and preoperative or intraoperative circumstances for preparing an acetabulum and guiding and implanting an acetabular implant along a preoperatively determined alignment orientation. In this respect, tools and instrumentation providing redundant functionality and of different embodiments may provide to the surgeon in a kit or per surgeon's request.

For example, adaptors and other instruments described above can be provided and used in various combinations within the scope of the methods described herein.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An acetabular guide system, comprising:
    an acetabular guide, including:
        an exterior surface configured to have a geometry to substantially engage the acetabulum of a specific patient;
        a central post extending from an interior surface of the acetabular guide;
        a second post extending from the interior surface of the acetabular guide substantially parallel to but offset relative to the central post along a radial direction; and
    a guide inserter having an elongated shaft defining an internal bore; wherein the internal bore of the elongated shaft is configured to engage an exterior surface of the central post to move the acetabular guide into the acetabulum.

2. The acetabular guide system of claim 1, wherein the exterior surface is curved to contact the acetabulum of a specific patient.

3. The acetabular guide system of claim 1, wherein the exterior surface is dome shaped.

4. The acetabular guide system of claim 1, wherein the central post extends away from the interior surface of the acetabular guide and is closed to an environment outside of the central post.

5. The acetabular guide system of claim 1, wherein the guide inserter includes at least a first finger to engage the second post when the central post is engaged within the internal bore of the guide inserter, wherein the guide inserter has rotational and axial control of the acetabular guide to position the acetabular guide within the acetabulum.

6. The acetabular guide system of claim 1, wherein the guide inserter includes an elongated portion with a handle and an inserter tip that is removable from the elongated portion.

7. The acetabular guide system of claim 1, wherein guide inserter tip includes a bore configured to engage the central post.

8. The acetabular guide system of claim 1, wherein the guide inserter includes first and second flanges that define an open channel that is configured to receive and hold the second post while the central post is received in the bore.

9. The acetabular guide system of claim 1, further comprising:
a pin guide defining a guide bore extending exterior to the interior surface; and
a guide line formed between the central post with the inserter engaged thereto and the guide bore, wherein the guide line is configured to be aligned with an inferior ischial spine of the specific patient due to the geometry of the exterior surface.

10. The acetabular guide system of claim 8, wherein the guide line is configured to be aligned with an inferior ischial spine of the specific patient due to the geometry of the exterior surface.

11. The acetabular guide system of claim 9, further comprising:
a pin guide insert defining an insert bore, wherein the pin guide insert is placed in the guide bore such that the insert bore is disposed on the guide line.

12. The acetabular guide system of claim 11, wherein the guide pin configured to be passed through the insert bore to engage a region of a pelvis superior to the acetabulum on the guide line.

13. An acetabular guide system, comprising:
an acetabular guide, including:
an exterior curved surface configured with a geometry to substantially match the acetabulum of a specific patient based on a geometry of the acetabulum of the specific patient;
a central post extending from an interior surface of the acetabular guide;
a second post extending from the interior surface of the acetabular guide substantially parallel to but offset relative to the central post along a radial direction; and
a guide inserter having an elongated shaft defining an internal bore, wherein the guide inserter includes a first finger to engage the second post when the central post is engaged within the internal bore of the guide inserter; wherein the internal bore of the elongated shaft is configured to engage an exterior surface of the central post to move the acetabular guide into the acetabulum and the guide inserter has rotational and axial control of the acetabular guide to position the acetabular guide within the acetabulum.

14. The acetabular guide system of claim 13, wherein the guide inserter includes a guide inserter tip having a bore configured to engage the central post.

15. The acetabular guide system of claim 13, wherein the first finger comprises first and second flanges that define an open channel that is configured to receive and hold the second post while the central post is received in the bore.

16. The acetabular guide system of claim 13, further comprising:
a pin guide defining a tapered guide bore having an internal tapered surface extending from the exterior curved surface;
a pin guide insert having an external tapered surface complementary with the internal tapered surface and defining an insert bore; and
a guide line that is defined by a first point on a first longitudinal axis through the central post and a second point on a second longitudinal axis through the pin guide, wherein guide pin is configured to pass through the insert bore and engage a region of a pelvis superior to the acetabulum on the guide line, and wherein positioning the acetabular guide within the acetabulum with the guide inserter aligns the insert bore along the guide line relative to an inferior ischial spine of the patient.

17. The acetabular guide system of claim 12, further comprising:
at least one registration hook extending from an acetabulum guide rim and formed to connect with the pin guide, wherein the registration hook is configured to contact near an acetabular rim when the exterior curved surface is engaged in the acetabulum.

18. An acetabular guide system, comprising:
an acetabular guide, including:
an exterior curved surface;
a central post extending from an interior surface of the acetabular guide;
a second post extending from the interior surface of the acetabular guide substantially parallel to but offset relative to the central post along a radial direction;
a pin guide defining a bore extending from the exterior curved surface;
a guide inserter having an elongated shaft defining an internal bore, wherein the guide inserter configured to engage at least one of the central post and the second post;
a pin guide insert configured to couple with the pin guide and defining an insert bore;
a guide line that is defined by a first point on a first longitudinal axis through the central post and a second point on a second longitudinal axis through the pin guide;
wherein the internal bore of the elongated shaft is configured to engage an exterior surface of the central post to move the acetabular guide into the acetabulum and the guide inserter has rotational and axial control of the acetabular guide to position the acetabular guide within the acetabulum and align the insert bore along the guide line relative to an inferior ischial spine of the patient.

19. The acetabular guide system of claim 18, wherein the guide inserter includes a first finger to engage the second post when the central post is engaged within the internal bore of the guide inserter.

20. The acetabular guide system of claim 19, wherein the first finger comprises first and second flanges that define an open channel that is configured to receive and hold the second post while the central post is received in the bore.

\* \* \* \* \*

UNITED STATES PATENT AND TRADEMARK OFFICE
CERTIFICATE OF CORRECTION

PATENT NO. : 9,597,201 B2  
APPLICATION NO. : 14/854497  
DATED : March 21, 2017  
INVENTOR(S) : Mark A. Bollinger Page 1 of 1

It is certified that error appears in the above-identified patent and that said Letters Patent is hereby corrected as shown below:

On the Title Page

In item (73), in "Assignee", in Column 1, Line 1, delete "LLC," and insert --LLC.,-- therefor On page 12, in Column 1, under "Other Publications", Line 41, delete "PMIImplants," and insert --PMI Implants,-- therefor On page 12, in Column 2, under "Other Publications", Line 41, delete "Sugery," and insert --Surgery,-- therefor In the Claims In Column 13, Line 39, in Claim 10, delete "claim 8," and insert --claim 9,-- therefor Signed and Sealed this  
Tenth Day of April, 2018

Andrei Iancu  
*Director of the United States Patent and Trademark Office*